US012716082B2

(12) United States Patent
Varman et al.

(10) Patent No.: US 12,716,082 B2
(45) Date of Patent: Aug. 25, 2026

(54) RECOMBINANT ENDOXYLANASES AND RELATED COMPOSITIONS AND METHODS OF USE

(71) Applicants: Arul Mozhy Varman, Chandler, AZ (US); Apurv Mhatre, Tempe, AZ (US)

(72) Inventors: Arul Mozhy Varman, Chandler, AZ (US); Apurv Mhatre, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 18/419,361

(22) Filed: Jan. 22, 2024

(65) Prior Publication Data

US 2024/0191274 A1 Jun. 13, 2024

Related U.S. Application Data

(62) Division of application No. 17/530,430, filed on Nov. 18, 2021, now abandoned.

(60) Provisional application No. 63/115,566, filed on Nov. 18, 2020.

(51) Int. Cl.

| | |
|---|---|
| *C12P 21/00* | (2006.01) |
| *C12N 1/20* | (2026.01) |
| *C12N 9/24* | (2006.01) |

(52) U.S. Cl.
CPC ................ *C12P 21/00* (2013.01); *C12N 1/20* (2013.01); *C12N 9/2402* (2013.01); *C12N 2500/10* (2013.01)

(58) Field of Classification Search
CPC ......... C12P 21/00; C12N 1/20; C12N 9/2402; C12N 2500/10
See application file for complete search history.

(56) References Cited

FOREIGN PATENT DOCUMENTS

CN 104928270 A * 9/2015

OTHER PUBLICATIONS

Zhang, Weiwei, et al. "Optimal secretion of alkali-tolerant xylanase in Bacillus subtilis by signal peptide screening." Applied Microbiology and Biotechnology 100 (2016): 8745-8756. (Year: 2016).*

(Continued)

*Primary Examiner* — Louise W Humphrey
*Assistant Examiner* — Candice Lee Swift
(74) *Attorney, Agent, or Firm* — FULLER IP LAW LLC; Rodney J. Fuller

(57) ABSTRACT

Disclosed are recombinant endoxylanases that are expressed and exported in high levels in bacteria, in particular *Bacillus subtilis*. The recombinant endoxylanases are based on an endoxylanase selected from *Trichoderma reesei* or *Bacillus pumilus* modified with a signal peptide from *B. subtilis* alpha amylase (AmyE), *B. subtilis* levanase (SacC), or *B. subtilis* YwmC. Accordingly, also disclosed are plasmids for transforming bacteria to express and export such recombinant endoxylanases and the resulting recombinant bacterial strains. The disclosure also encompasses compositions for simultaneously degrading and assimilate cellobiose and xylan comprising a recombinant bacteria engineered to produce xylose from hydrolyzing the agricultural biomass and a xylose assimilator and methods of producing value-added products, for example succinate, from agricultural biomass using such compositions.

5 Claims, 6 Drawing Sheets

Specification includes a Sequence Listing.

(56) References Cited

OTHER PUBLICATIONS

Panbangred, Watanalai, et al. "Expression of a xylanase gene of Bacillus pumilus in *Escherichia coli* and Bacillus subtilis." Applied microbiology and biotechnology 22 (1985): 259-264. (Year: 1985).*
KEGG; https://www.genome.jp/dbget-bin/www_bget?ec:3.2.1.8; accessed Feb. 21, 2025 (Year: 2025).*
Kapilan, Ranganathan, and Vasanthy Arasaratnam. "Improvement of Bacillus pumilus for higher Xylanase production by mutation." (2015). (Year: 2015).*
Qu, Wei, and Weilan Shao. "Cloning, expression and characterization of glycoside hydrolase family 11 endoxylanase from Bacillus pumilus ARA." Biotechnology letters 33 (2011): 1407-1416. (Year: 2011).*
Caspers, Michael, et al. "Improvement of Sec-dependent secretion of a heterologous model protein in Bacillus subtilis by saturation mutagenesis of the N-domain of the AmyE signal peptide." Applied microbiology and biotechnology 86 (2010): 1877-1885. (Year: 2010).*
Freudl, Roland. "Signal peptides for recombinant protein secretion in bacterial expression systems." Microbial cell factories 17.1 (2018): 52. (Year: 2018).*
GenBank AAS18312.1; https://www.ncbi.nlm.nih.gov/protein/AAS18312.1/; accessed Jun. 30, 2025 (Year: 2004).*
Fukusaki, Eiichiro, et al. "The complete nucleotide sequence of the xylanase gene (xynA) of Bacillus pumilus." FEBS letters 171.2 (1984): 197-201. (Year: 1984).*
Wang, Jing, et al. "An alkali-tolerant xylanase produced by the newly isolated alkaliphilic Bacillus pumilus from paper mill effluent." Molecular biology reports 37 (2010): 3297-3302. (Year: 2010).*
GenBank ACH67614.1; https://www.ncbi.nlm.nih.gov/protein/ACH67614.1/; accessed Jun. 30, 2025 (Year: 2010).*
GenBank ADK27486.1; https://www.ncbi.nlm.nih.gov/protein/ADK27486.1/; accessed Jun. 30, 2025 (Year: 2011).*

* cited by examiner

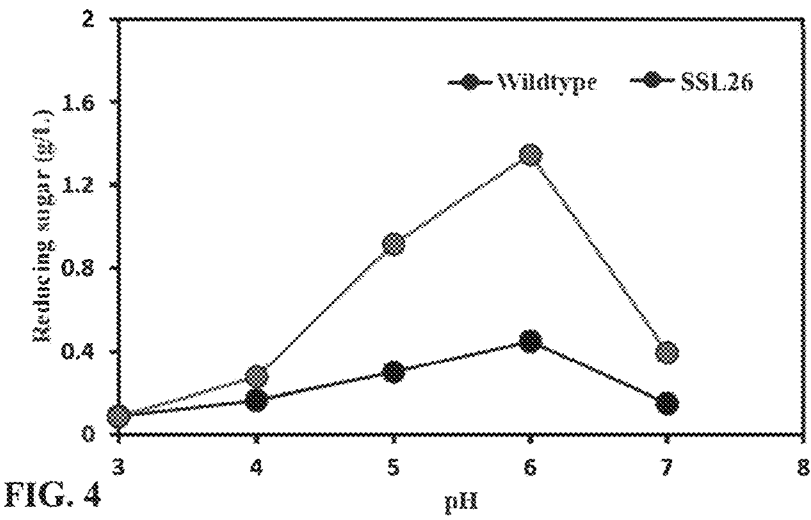
FIG. 4
FIG. 5
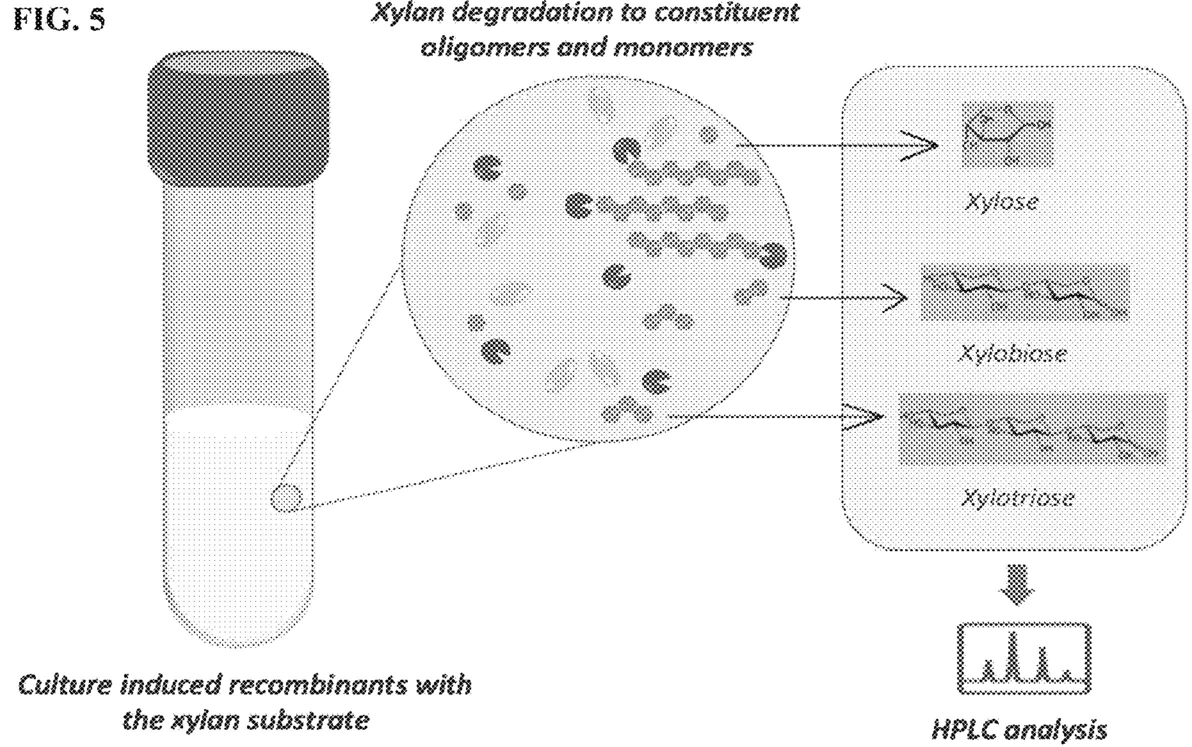

Xylose (g/L)
16
12
8
4
0
Chen et al., 2010
Zhao et al., 2012
Yuan et al., 2019
Zin et al., 2018
Present study (1% Xylan)
Present study (5% Xylan)

Succinate producer
Xylose producer
B. Subtilis and E. coli coculture
Succinate

E: B – E. coli $OD_{600}$ / B. Subtilis $OD_{600}$

RECOMBINANT ENDOXYLANASES AND RELATED COMPOSITIONS AND METHODS OF USE

CROSS-REFERENCE TO RELATED APPLICATIONS

This application is a divisional application of U.S. utility application Ser. No. 17/530,430, filed Nov. 18, 2021, titled "RECOMBINANT ENDOXYLANASES AND RELATED COMPOSITIONS AND METHODS OF USE," which claims the benefit of and priority to U.S. provisional application No. 63/115,566, filed Nov. 18, 2020, titled "RECOMBINANT *BACILLUS SUBTILIS* STRAIN AND METHODS OF USE THEREOF," the contents of which are incorporated herein by reference in its entirety.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 10,941-byte XML file named "SeqList_072" created on Jan. 22, 2024.

FIELD OF THE INVENTION

The invention relates to recombinant *Bacillus subtilis* that can simultaneously degrade and assimilate cellobiose and xylan.

BACKGROUND OF THE INVENTION

Advent of the 21st century has seen surge in demand of energy, the depletion of fossil fuel reserves and detrimental effect of fossil fuels on environment. Therefore, alternative energy sources have been extensively explored to reduce our dependence on non-renewable fuel sources. Agricultural field waste (also referred to herein as "agricultural biomass") has been considered to be the most abundant energy source and extensive efforts are invested worldwide for valorizing it. Agricultural biomass is mainly made of the biopolymers cellulose, hemicellulose, and lignin. Agricultural biomass is rich renewable source and different methods have been used like pyrolysis, gasification, hydrolysis, etc. to explore its potential as energy and chemical source. For example, hemicellulosic and cellulosic agricultural waste is a promising renewable feedstock for increasing future demand of renewable biofuels and value-added products.

Hydrolysis of biomass can be done mainly by a chemical or an enzymatic route. The enzymatic route is more environmentally friendly and efficient than the chemical route due to the conversion efficiency of enzymes. However, commercial enzymes are expensive to use. The expense can be a big discouraging factor as the goal of processing agricultural wastes is to find a low-cost alternative. Accordingly, alternative processing method of agricultural waste using the enzymatic route is needed to take advantage of the efficiency of the enzymes while keeping costs low.

SUMMARY OF THE INVENTION

The disclosure also relates to plasmids for making recombinant bacteria that express and export an enzyme for xylan degradation (an endoxylanase). In some aspects, the plasmid is used for transforming *Corynebacterium glutamicum*, *Bacillus subtilis*, or *Bacillus coagulans* so that they express and export an endoxylanase selected from *Trichoderma reesei* or *Bacillus pumilus* or a variant thereof. The endoxylanase or variant thereof from *T. reesei* or *B. pumilus* are modified with a signal peptide selected from *B. subtilis* alpha amylase signal peptide (AmyE), *B. subtilis* levanase signal peptide (SacC), and *B. subtilis* YwmC signal peptide, or a variant thereof. In some embodiments, the plasmid comprises a sequence encoding a signal peptide selected from the group consisting of: AmyE, SacC, YwmC, and a variant thereof, and a sequence encoding an endoxylanase selected from *T. reesei* or *Bacillus pumilus* or a variant thereof, wherein the sequence encoding the signal peptide is upstream of the sequence encoding the endoxylanase thereby producing a recombinant endoxylanase modified with the signal peptide. The amino acid sequence of the variant AmyE encoded by the sequence encoding the signal peptide has at least 80% identity to SEQ ID NO:1. The amino acid sequence of the variant SacC encoded by the sequence encoding the signal peptide has at least 80% identity to SEQ ID NO:2. The amino acid sequence of the variant YwmC encoded by the sequence encoding the signal peptide has at least 80% identity to SEQ ID NO:3.

In certain embodiments, the amino acid sequence of the endoxylanase or variant thereof encoded by the sequence encoding the endoxylanase has at least 90% sequence identity to SEQ ID NO:4. In such embodiments, the amino acid sequence of the variant signal peptide encoded by the sequence encoding the signal peptide has at least 90% sequence identity to SEQ ID NO: 1, SEQ ID NO:2, or SEQ ID NO:3. In particular embodiments, the amino acid sequence of the recombinant endoxylanase is set forth in SEQ ID NO:6. For example, the amino acid sequence encoded by the plasmid is set forth in SEQ ID NO:7.

In other embodiments, the sequence encoding the endoxylanase or variant thereof has at least 90% sequence identity to SEQ ID NO:5. In such embodiments, the sequence encoding the signal peptide has at least 90% sequence identity to SEQ ID NO: 1, SEQ ID NO:2, or SEQ ID NO:3. In particular embodiments, the sequence encoding the signal peptide is set forth in SEQ ID NO:1, SEQ ID NO:2, or SEQ ID NO:3. In certain embodiments, the sequence encoding the endoxylanase is set forth in SEQ ID NO:5.

The disclosure also relates to compositions and methods of consolidated bioprocessing of plant biomass. The compositions comprise a recombinant bacteria engineered to produce xylose from hydrolyzing the agricultural biomass and a xylose assimilator. The recombinant bacteria engineered to produce xylose from hydrolyzing the agricultural biomass is selected from the group consisting of: *C. glutamicum, B. subtilis*, and *B. coagulans*. In some aspects, the recombinant bacteria engineered to produce xylose from hydrolyzing the agricultural biomass has been transformed with a plasmid described herein. The xylose assimilator is a bacterium selected from the group consisting of: *Escherichia coli, B. coagulans, Lactobacillus pentosus, Lactobacillus brevis, Leuconostoc lactis*, a different strain of *B. coagulans* than the xylose producer, and a different strain of *B. subtilis* than the xylose producer. In some embodiments, the composition further comprises a media comprising a trace metal solution and M9 media, wherein the trace metal solution comprises sulfate salts of copper, irone, zinc, and magnesium and the M9 media comprises $KH_2PO_4$, $Na_2HPO_4$, NaCl, $NH_4Cl$, glucose, tryptophan, and citrate.

In some aspects, the compositions comprise recombinant bacteria engineered to produce xylose from hydrolyzing the agricultural biomass is *B. subtilis*. Thus, in certain embodiments, the composition comprises a recombinant *B. subtilis* engineered to produce xylose from hydrolyzing the agricultural biomass and *E. coli* as the xylose assimilator. In some aspects, the xylose assimilator is a succinate producer.

The methods of producing value-added products from agricultural biomass comprises providing an agricultural biomass, wherein the agricultural biomass comprises xylan; adding a culture of a xylose producer to the agricultural biomass, wherein the xylose producer is a recombinant bacteria engineered to produce xylose from hydrolyzing the agricultural biomass; and adding a culture of a xylose assimilator to the agricultural biomass. The recombinant bacteria are selected from the group consisting of: *C. glutamicum, B. subtilis*, and *B. coagulans*. In certain implementations, the recombinant bacteria have been transformed with a plasmid described herein. The xylose assimilator is a bacterium selected from the group consisting of: *E. coli, B. coagulans, L. pentosus, L. brevis, L. lactis*, a different strain of *B. coagulans* than the xylose producer, and a different strain of *B. subtilis* than the xylose producer. In certain implementations, the recombinant bacteria engineered to produce xylose from hydrolyzing the agricultural biomass is a recombinant *B. subtilis*. In some aspects, the corresponding xylose assimilator is *E. coli.*

BRIEF DESCRIPTION OF THE DRAWINGS

FIG. 4 depicts, in accordance with certain embodiments, the results of a xylan depolymerization study using SSL26.

FIG. 5 depicts, in accordance with certain embodiments, a scheme of in situ breakdown of xylan using the systems or according to the methods described herein.

DETAILED DESCRIPTION OF THE INVENTION

Figure 1:
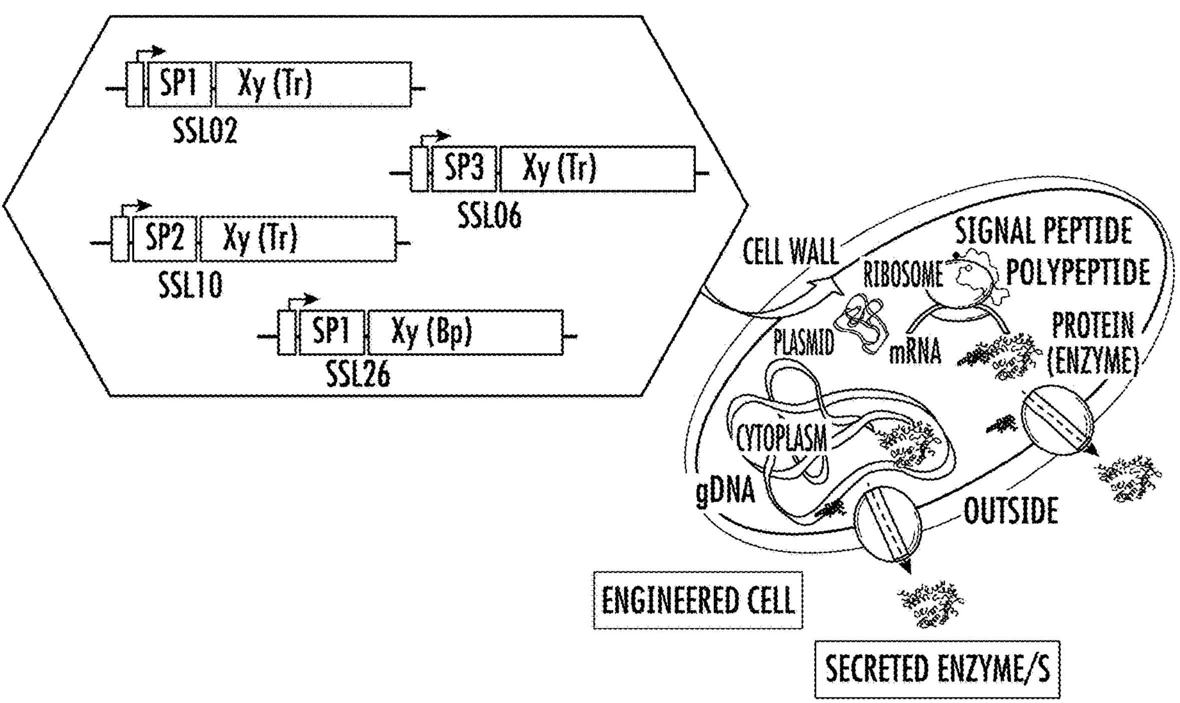
FIG. 1 depicts, in accordance with certain embodiments, exemplary recombinant strains of *Bacillus subtilis* described herein that enable production and export of endoxylanases. Abbreviations in figure: SP1 refers to YwmC, SP2 refers to AmyE, SP3 refers to SacC, Xy(Tr) refers to Xyn2 from *Trichoderma reesei*, Xy(Bp) refers to XynA from *Bacillus pumilus.*

Detailed aspects and applications of the invention are described below in the drawings and detailed description of the invention. Unless specifically noted, it is intended that the words and phrases in the specification and the claims be given their plain, ordinary, and accustomed meaning to those of ordinary skill in the applicable arts.

In the following description, and for the purposes of explanation, numerous specific details are set forth to provide a thorough understanding of the various aspects of the invention. It will be understood, however, by those skilled in the relevant arts, that the present invention may be practiced without these specific details. It should be noted that there are many different and alternative configurations, devices, and technologies to which the disclosed inventions may be applied. The full scope of the inventions is not limited to the examples that are described below.

The singular forms "a," "an," and "the" include plural referents unless the context clearly dictates otherwise. Thus, for example, reference to "a step" includes reference to one or more of such steps.

The term "variant" as used herein refers to a variation in the amino acid sequence where the resulting variant amino acid product has at least 80% sequence homology to the original or reference amino acid sequence. In some aspects, the amino acid sequence of the variant amino has at least 85%, at least 90%, at least 95%, at least 96%, at least 97%, at least 98%, at least 99%, at least 99.5%, or at least 99.9% sequence homology to the original or reference amino acid sequence. In some aspects, the amino acid sequence of the variant has at least 85%, at least 90%, at least 95%, at least 96%, at least 97%, at least 98%, at least 99%, at least 99.5%, or at least 99.9% sequence identity to the original or reference amino acid sequence. In certain embodiments, the amino acid sequence of the variant has less than 8, less than 7, less than 6, or less than 5 insertions, deletions, and/or substitutions when compared the original or reference amino acid sequence.

Plant biomass is the largest source of carbon on the planet. This huge resource if efficiently utilized can be useful in providing an alternative option to non-renewable sources. Different methods have been used for plant biomass utilization previously and enzymatic degradation is effective due to its high specificity. Signal peptides are short chain polypeptides which play a vital role in enzyme export. Efficient and cost-effective methods are essential for breakdown of cellulosic materials into elementary components. Cost effective enzymatic hydrolysis of the cellulosic and hemicellulosic biomass can play a vital role in making economical biorefineries viable. The disclosure relates to a process of converting agricultural biomass. Instead of using commercial enzymes, the described process aims at engineering bacteria to export enzymes that hydrolyze the biomass during a fermentation process to produce commercially viable products, for example xylose and succinate. Xylan and cellobiose are two chemicals which are formed by polymerization of sugar like glucose, xylose, arabinose, rhamnose, and these sugars can be consumed by bacterial cells as energy source. Accordingly, disclosed herein are plasmids for making recombinant bacteria, such as *Bacillus subtilis*, that breakdown hemicellulose (for example xylan) into simple sugars. The plasmids described herein enable the expression and export of an endoxylanase from *Trichoderma reesei* or *Bacillus pumilus* or a variant thereof. In addition to the transformation of *B. subtilis*, the plasmid may also be used for transforming *Corynebacterium glutamicum* or *Bacillus coagulans* into recombinant bacteria that express and export an endoxylanase from *Trichoderma reesei* or *Bacillus pumilus* or a variant thereof. To enable the export of the expressed endoxylanase, the enzyme is modified with a signal peptide from selected from *B. subtilis* alpha amylase signal peptide (AmyE), *B. subtilis* levanase signal peptide (SacC), and *B. subtilis* YwmC signal peptide, or a variant thereof.

Thus, described herein are plasmids comprising a sequence encoding a signal peptide selected from the group consisting of: AmyE, SacC, YwmC, and a variant thereof, and a sequence encoding an endoxylanase selected from *Trichoderma reesei, Bacillus pumilus*, or a variant thereof, wherein the sequence encoding the signal peptide is upstream of the sequence encoding the endoxylanase thereby producing a recombinant endoxylanase modified with the signal peptide. The endoxylanase from *T. reesei* has an amino acid sequence set forth in SEQ ID NO:5, while the endoxylanase from *B. pumilus* has an amino acid sequence set forth in SEQ ID NO:4. The variant endoxylanase from *T. reesei* has an amino acid sequence with at least at least 80%, at least 85%, at least 90%, at least 95%, at least 96%, at least 97%, at least 98%, at least 99%, at least 99.5%, or at least 99.9% homology to SEQ ID NO:5. In some aspects, the variant endoxylanase from *T. reesei* has an amino acid sequence with at least at least 80%, at least 85%, at least 90%, at least 95%, at least 96%, at least 97%, at least 98%, at least 99%, at least 99.5%, or at least 99.9% identity to SEQ ID NO:5. The variant endoxylanase from *B. pumilus* has an amino acid sequence with at least at least 80%, at least 85%, at least 90%, at least 95%, at least 96%, at least 97%, at least 98%, at least 99%, at least 99.5%, or at least 99.9% homology to SEQ ID NO:4. In some aspects, the variant endoxylanase from *B. pumilus* has an amino acid sequence with at least at least 80%, at least 85%, at least 90%, at least 95%, at least 96%, at least 97%, at least 98%, at least 99%, at least 99.5%, or at least 99.9% identity to SEQ ID NO:4.

The amino acid sequence of the variant AmyE encoded by the sequence encoding the signal peptide has at least 80%, at least 85%, at least 90%, at least 95%, at least 96%, at least 97%, at least 98%, at least 99%, at least 99.5%, or at least 99.9% identity to SEQ ID NO:1. In some aspects, the amino acid sequence of the variant AmyE encoded by the sequence encoding the signal peptide has at least 80%, at least 85%, at least 90%, at least 95%, at least 96%, at least 97%, at least 98%, at least 99%, at least 99.5%, or at least 99.9% homology to SEQ ID NO:1. The amino acid sequence of the variant SacC encoded by the sequence encoding the signal peptide has at least 80%, at least 85%, at least 90%, at least 95%, at least 96%, at least 97%, at least 98%, at least 99%, at least 99.5%, or at least 99.9% identity to SEQ ID NO:2. In some aspects, the amino acid sequence of the variant SacC encoded by the sequence encoding the signal peptide has at least 80%, at least 85%, at least 90%, at least 95%, at least 96%, at least 97%, at least 98%, at least 99%, at least 99.5%, or at least 99.9% homology to SEQ ID NO:2. The amino acid sequence of the variant YwmC encoded by the sequence encoding the signal peptide has at least 80%, at least 85%, at least 90%, at least 95%, at least 96%, at least 97%, at least 98%, at least 99%, at least 99.5%, or at least 99.9% identity to SEQ ID NO:3. In some aspects, the amino acid sequence of the variant YwmC encoded by the sequence encoding the signal peptide has at least 80%, at least 85%, at least 90%, at least 95%, at least 96%, at least 97%, at least 98%, at least 99%, at least 99.5%, or at least 99.9% homology to SEQ ID NO:3.

In certain embodiments, the amino acid sequence of the endoxylanase or variant thereof encoded by the sequence encoding the endoxylanase has at least 90% sequence identity to SEQ ID NO:4. In such embodiments, the amino acid sequence of the variant signal peptide encoded by the sequence encoding the signal peptide has at least 90% sequence identity to SEQ ID NO: 1, SEQ ID NO:2, or SEQ ID NO:3. In particular embodiments, the amino acid sequence of the recombinant endoxylanase is set forth in SEQ ID NO:6. For example, the amino acid sequence of the plasmid is set forth in SEQ ID NO:7. Also described are the recombinant bacteria that express the plasmids described herein, for example, a plasmid having an amino acid sequence set forth in SEQ ID NO:7. In certain embodiments, the recombinant bacteria is *C. glutamicum, B. subtilis*, or *B. coagulans.*

The recombinant bacteria described herein can break-down the biopolymers found in plant biomass in a one-pot process. Accordingly, a one-pot fermentation system to process agricultural waste product involving a polymer degradation process are also described, and the disclosure also relates to compositions and methods of consolidated bioprocessing of plant biomass. The end products of the one-pot fermentation system to process agricultural biomass produces can be a wide range of useful products, like succinate, ethanol, lactate, etc. The composition and methods relate to bacterial digestion of agricultural biomass, for example, the breakdown of hemicellulose into simple sugars by bacteria, for example, the breakdown of xylan into xylose and then further into value-added products, such as succinate, ethanol, or lactate. Accordingly, the described system and method for processing agricultural biomass can also help reduce the production cost value-added products from agricultural biomass.

The compositions comprise a recombinant bacteria engineered to produce xylose from hydrolyzing the agricultural biomass and a xylose assimilator. The recombinant bacteria engineered to produce xylose from hydrolyzing the agricultural biomass is selected from the group consisting of: *C. glutamicum, B. subtilis*, and *B. coagulans*. In some aspects, the recombinant bacteria engineered to produce xylose from hydrolyzing the agricultural biomass has been transformed with at least one plasmid described herein. The xylose assimilator is a bacterium selected from the group consisting of: *Escherichia coli, B. coagulans, Lactobacillus pentosus, Lactobacillus brevis, Leuconostoc lactis*, a different strain of *B. coagulans* than the xylose producer, and a different strain of *B. subtilis* than the xylose producer. In some aspects, the compositions comprise recombinant bacteria engineered to produce xylose from hydrolyzing the agricultural biomass is *B. subtilis*. Thus, in certain embodiments, the composition comprises a recombinant *B. subtilis* engineered to produce xylose from hydrolyzing the agricultural biomass and *E. coli* as the xylose assimilator. In some aspects, the xylose assimilator is a succinate producer.

Hydrolysis reaction mainly involves lysis of the long biopolymeric chains in reaction mixture predominantly consisting of water. The polymer degradation comprises a first step involving xylan degradation and a second step involving cellobiose degradation. Both steps involve using different signal peptides. For xylan degradation, the best results were displayed by the recombinant endoxylanase YwMC- XynA with an amino acid sequence set forth in SEQ ID NO:6. The highest yields obtained were 6.7 g/L of xylose from 1% xylan.

In some embodiments, the composition further comprises a media designed for in situ breakdown of the polymers. This media comprises: a trace metal solution and M9 media. In some aspects, the media further comprises $CaCl_2$). In some aspects, the media pH is adjusted to 6, for example with sodium phosphate and citric acid. In a particular embodiment, the one-pot fermentation system comprises the following in 5 ml of the media:

M9 media (10×) 0.5 ml
Trace metal solution (1000×) 5 ul
CaCl2 0.5 ul
Chloramphenicol 5 ug/ml
Seed culture $OD_{600}$ of 1.7 50 ul.

The trace metal solution comprises sulfate salts of copper, irone, zinc, and magnesium. In some embodiments, the trace metal solution (1000×) has the following components:

$CuSO_4$ 60 mM
$FeSO_4$ 60 mM
$ZnSO_4$ 60 mM
$MgSO_4$ 2000 mM

The M9 media comprises $KH_2PO_4$, $Na_2HPO_4$, NaCl, $NH_4Cl$, glucose, tryptophan, and citrate. In some embodiments, M9 media (10×) has the following components:

$KH_2PO_4$—0.6 g in 100 ml
$Na_2HPO_4$—3.21 g in 100 ml
NaCl—0.5 g in 100 ml
$NH_4Cl$—1 g in 100 ml
Glucose—20 g in 100 ml
Tryptophan—50 g in 100 ml
Citrate—1.79 g in 100 ml The methods of producing value-added products from agricultural biomass comprises providing an agricultural biomass, wherein the agricultural biomass comprises xylan; adding a culture of a xylose producer to the agricultural biomass, wherein the xylose producer is a recombinant bacteria engineered to produce xylose from hydrolyzing the agricultural biomass; and adding a culture of a xylose assimilator to the agricultural biomass. The recombinant bacteria are selected from the group consisting of: *C. glutamicum, B. subtilis*, and *B. coagulans*. In certain implementations, the recombinant bacteria have been transformed with a plasmid described herein. The xylose assimilator is a bacterium selected from the group consisting of: *E. coli, B. coagulans, L. pentosus, L. brevis, L. lactis*, a different strain of *B. coagulans* than the xylose producer, and a different strain of *B. subtilis* than the xylose producer. In certain implementations, the recombinant bacteria engineered to produce xylose from hydrolyzing the agricultural biomass is a recombinant *B. subtilis*. In some aspects, the corresponding xylose assimilator is *E. coli.*

In some aspects, the cultures of the xylose producer or the xylose assimilator comprise the above-described media designed for in situ breakdown of the polymers.

The disclosed process has the highest pentose sugar yields compared to pre-existing processes. It is also cost effective and environment friendly compared to other hydrolysis methods.

Illustrative, Non-Limiting Examples in Accordance with Certain Embodiments

The disclosure is further illustrated by the following examples that should not be construed as limiting. The contents of all references, patents, and published patent applications cited throughout this application, as well as the Figures, are incorporated herein by reference in their entirety for all purposes.

1) Screening of Recombinant Strains Containing Signal Peptides and Enzymes Showing Highest Hydrolysis Activity A DNS assay was used for evaluating endo-1,4-β-xylanase activity in the supernatant of the recombinant *B. subtilis* culture. The recombinant *B. subtilis* strain tested were genetically engineered to express an endoxylanase modified with a signal peptide from the alpha amylase of *B. subtilis* (AmyE, SEQ ID NO:1), from the levanase of *B. subtilis* (SacC, SEQ ID NO:2), or the YwmC protein of *B. subtilis* (SEQ ID NO: 3). FIG. 1 depicts four exemplary strains.

Figure 2:
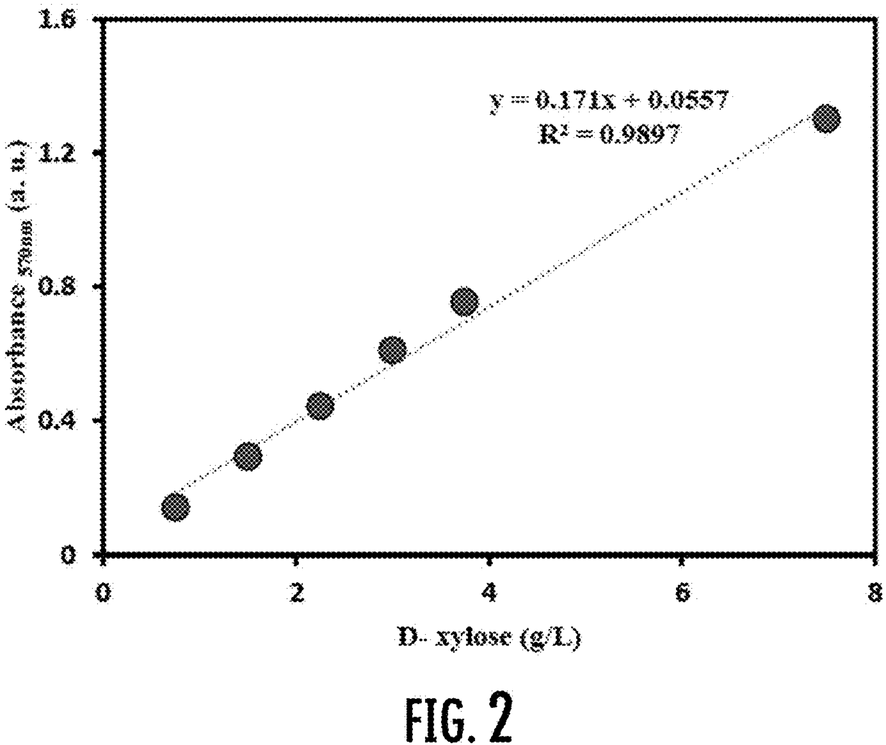
FIG. 2 depicts, in accordance with certain embodiments, an exemplary standard curve for convert the absorbance measurements into reducing sugar concentrations for a DNS assay.

Engineered *B. subtilis* strains were grown in 5 mL of 2×YT media until the early logarithmic growth phase ($OD_{600=0.8}$) at 37° C. and 250 rpm and induced with 1 mM isopropyl β-D-1-thiogalactopyranoside (IPTG) at the exponential phase for expression and secretion of the target enzyme. The strains were grown further for 24 hours to accumulate endo-1,4-β-xylanase in the extracellular media and supernatant samples were collected to be used for enzyme reactions. Birchwood xylan (1% w/v) in citrate phosphate buffer (20 μL) (pH adjusted as required) was mixed with supernatants (20 μL) containing the secreted enzyme at a 1:1 volume ratio in a flat bottom 96-well plate to a total volume of 40 μL and was incubated at 50° C. for 5, 10, 15, 30, and 60 mins to understand the kinetics of xylan depolymerization. The amount of reducing sugar produced through the action of endo-1,4-β-xylanase on xylan was estimated using 3, 5 dinitrosalicyclic acid (DNS) assay. The enzyme reaction was ended by adding 160 μL of DNS and by heating at 105° C. for 20 mins. Color change at the end of the DNS reaction was measured at an absorbance of 570 nm. A standard curve was used to convert the absorbance measurements into reducing sugar concentrations (FIG. 2).

Figure 3A:
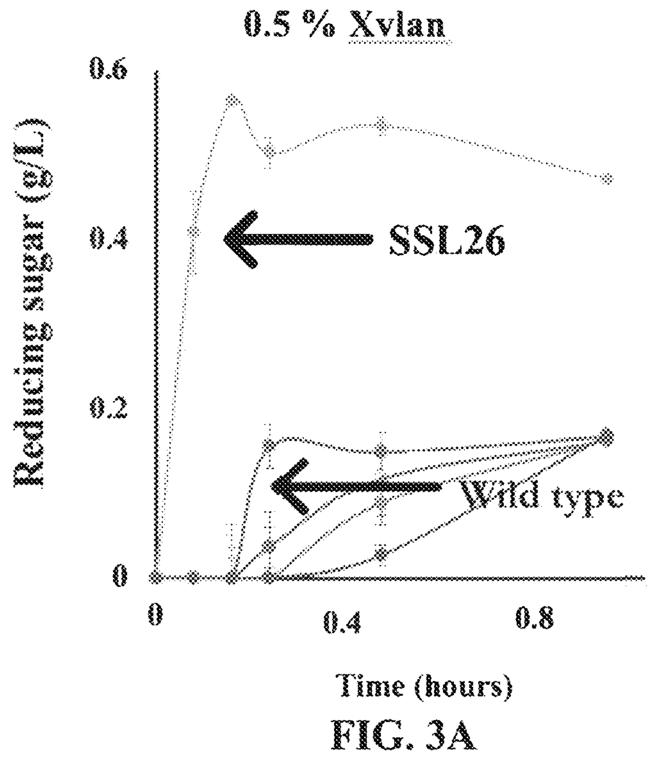
FIGS. 3A and 3B depict, in accordance with certain embodiments, the sugar reducing capabilities of the SSL26 strain in the presence of varying concentrations of xylan.
Figure 3B:
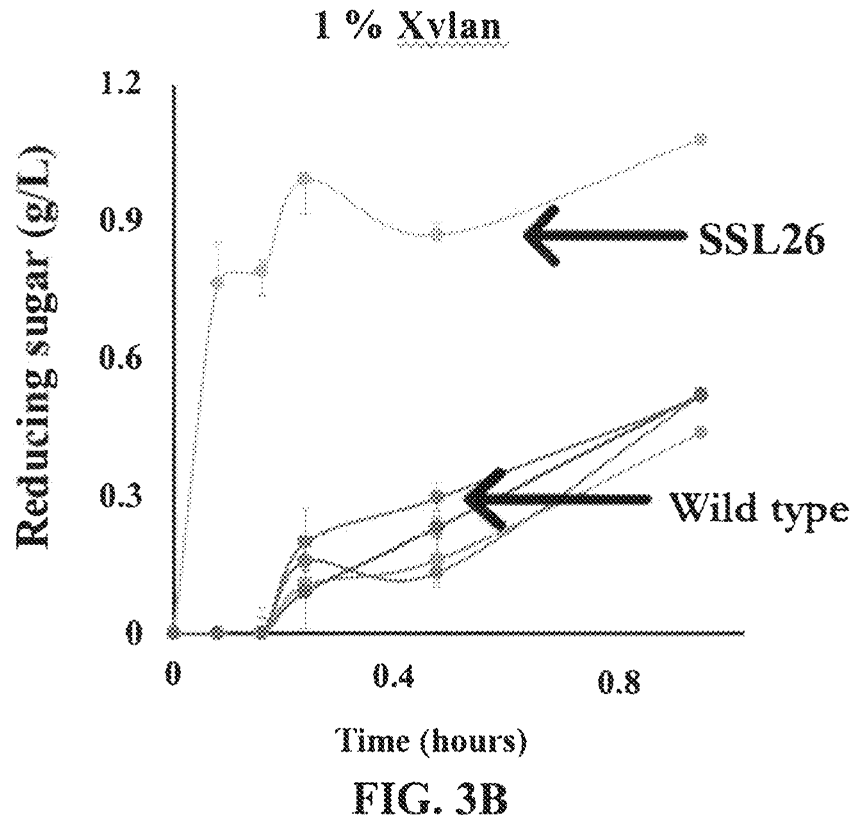

The SSL26 strain, which is genetically engineered to express the enodxylanase from *B. Pumilus* modified with the signal peptide of the YwmC protein of *B. subtilis*, resulted in the highest hydrolysis activity (FIGS. 3A and 3B).

2) In Situ Hemicellulose Depolymerization

Xylan depolymerization studies were conducted in 3M media with starting pH of 6.0 as it was found to be optimal for the endo-1,4-β-xylanase activity (FIG. 4). Engineered strains were grown in 3M media with 1.30% xylan at 37° C. and 250 rpm for 4 hours. The strains were induced with 0, 0.1, 0.2, 1 and, 2 mM IPTG to express and secrete the xylanase enzyme. Following induction, xylan depolymerization was carried out at 37° C. for 4 days. The fermentation batches were sampled at 24, 48, 72, and 96 hrs after IPTG induction for $OD_{600}$ measurement as well as for the quantification of, substrate and product concentrations using HPLC (FIG. 5).

Figure 6A:
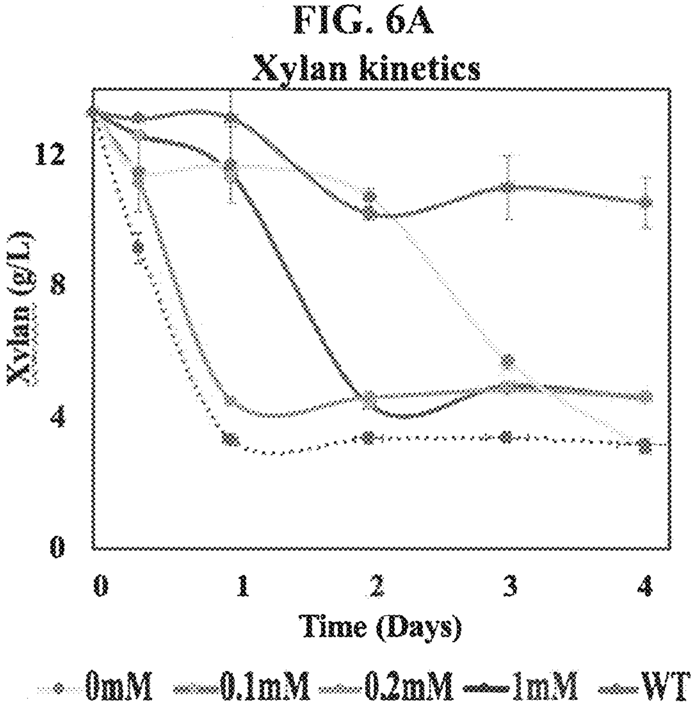
FIGS. 6A and 6B depict, in accordance with certain embodiments, the kinetics of the xylan (FIG. 6A) and xylose (FIG. 6B) reactions from the SSL26 strain.
Figure 6B:
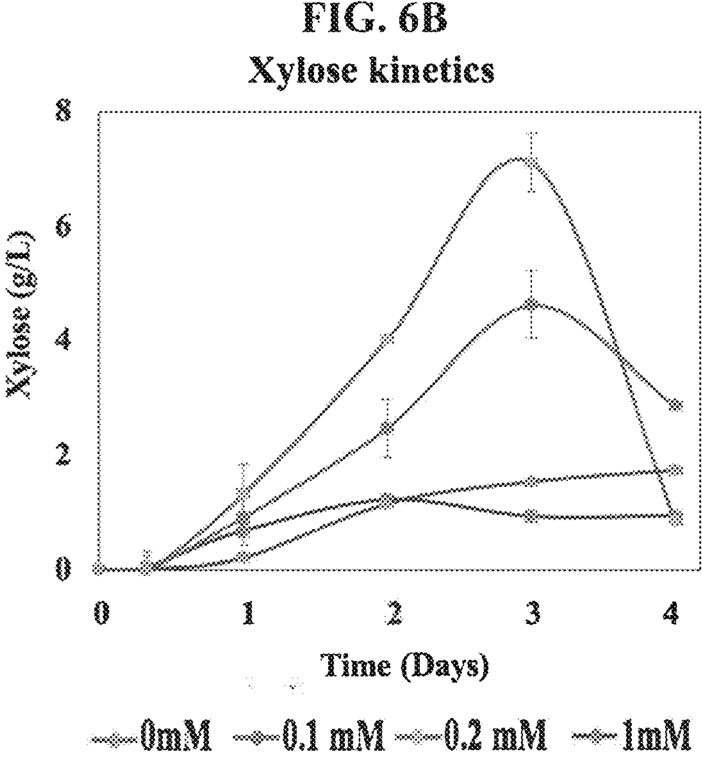

As shown in FIG. 6B, higher expression of the endoxylanase (induced by greater concentrations of IPTG) does not necessarily result in the highest production of xylose. As such, too high expression of the enzyme can negatively affect the export of the enzyme by the bacteria. The optimal concentration of IPTG to induce expression of the endoxylanase in the best strain of *B. subtilis* described herein is 0.2 mM.

Figure 7:
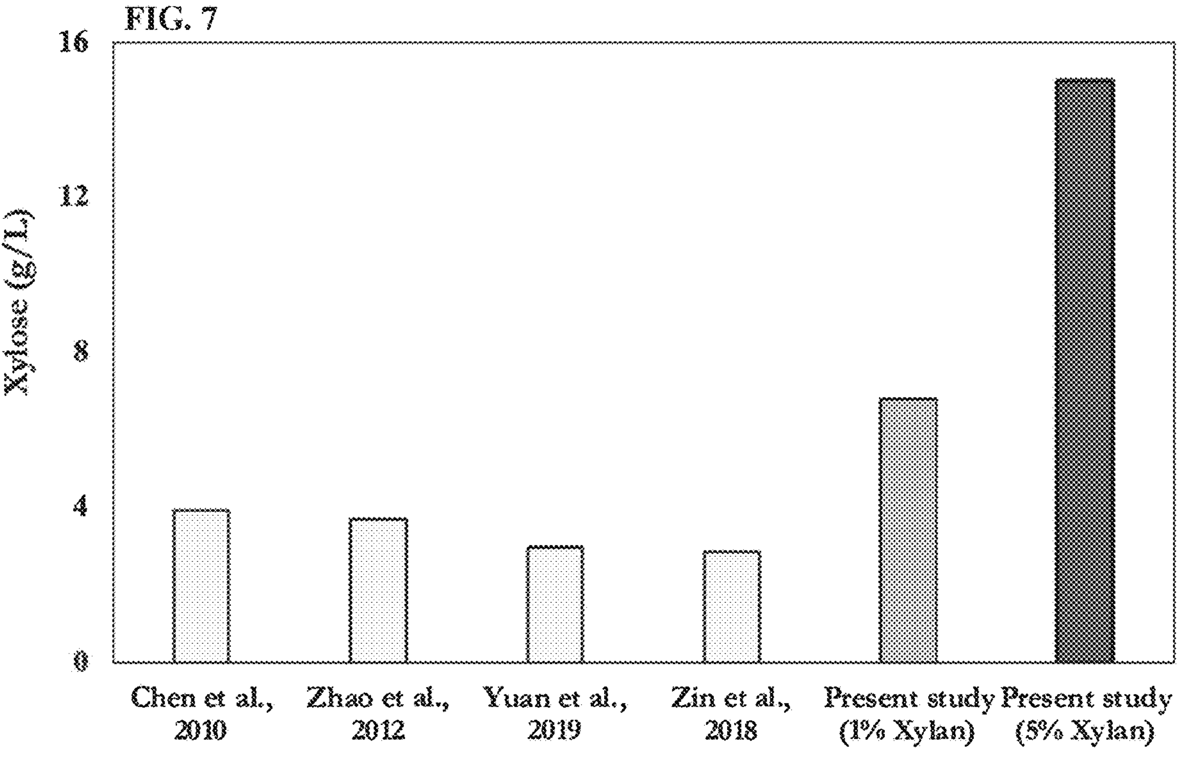
FIG. 7 depicts, in accordance with certain embodiments, a comparison of the xylose production of the SSL26 strain versus other strains, or bacteria described in the specified prior art. The prior art references all reported xylose production from medium containing 1% xylan. The prior art references are Tsai et al., *Applied and Environmental Microbiology,* 2010, 76, 7514-7520 (described in the figure as Chen et al., 2010); Zheng et al., *Microbial Cell Factories,* 2012, 11, 1-11 (Zhao et al., 2012); Liu et al., *Bioresource Technology,* 2019, 292, 121965-121965 (Yuan., 2019); and Jiang et al., *Biotechnology for Biofuels,* 2018, 11, 89 (Xin et al., 2018).

As shown in FIG. 7, xylose production from medium containing 1% xylan of the SSL26 strain when compared to other strains, or bacteria described in the prior art (Tsai et al., *Applied and Environmental Microbiology,* 2010, 76, 7514-7520; Zheng et al., *Microbial Cell Factories,* 2012, 11, 1-11; Liu et al., *Bioresource Technology,* 2019, 292, 121965-

121965; and Jiang et al., *Biotechnology for Biofuels,* 2018, 11, 89) is at least about two times greater.

Figure 8:
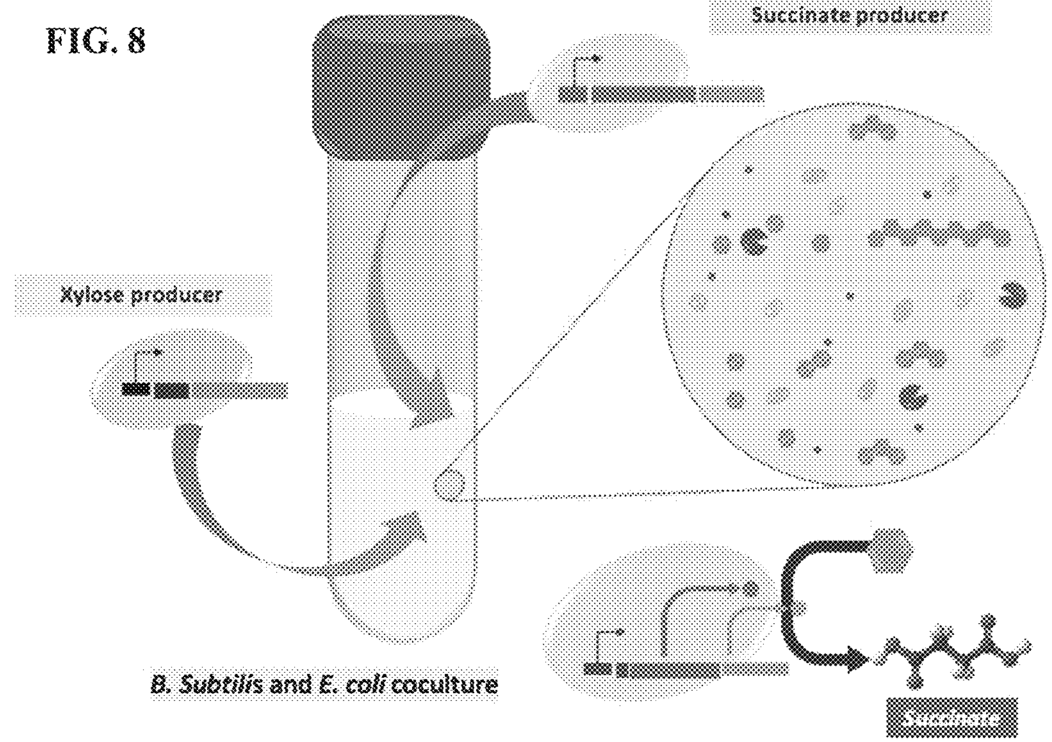
FIG. 8 depicts, in accordance with certain embodiments, a scheme of a coculture process for producing succinate.
Figure 9:
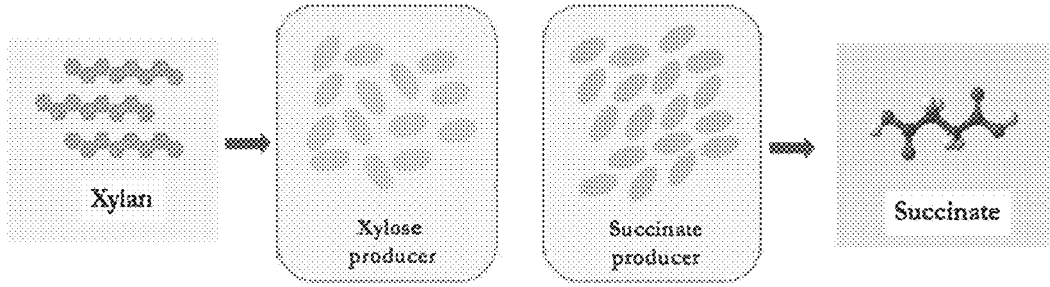
FIG. 9 depicts, in accordance with certain embodiments, succinate production using the coculture systems or according to the methods described herein. "E" represents the amount of *Escherichia coli* reported as $OD_{600}$. B represents the amount of the recombinant *B. subtilis* reported as $OD_{600}$.
Figure 9:
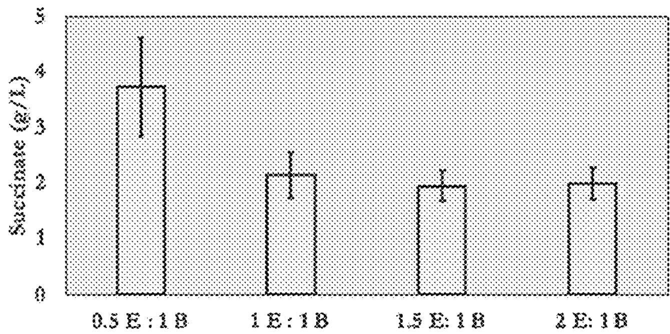

3) Coculture Cultivation for the Consolidated Bioprocessing of Xylan to Succinate Consolidated bioprocessing (CBP) refers to the combination of multiple biological events required to convert a starting material into a desired end product in a one-pot reaction. For CBP of xylan to succinate, the multiple biological events include the production of xylose from xylan and the metabolism of xylose into succinate (FIG. 9). The first successful CBP of xylan to succinate using a coculture of a *B. subtilis* xylose producer and a succinate producer that is a different species of bacteria is described in this example (FIG. 8).

The seed culture of the *B. subtilis* strain SSL26 was grown overnight in glass culture tubes in 2×YT media, shaking at 250 rpm at 37° C. The next day, 50 μL of seed culture was added to 5 mL of 3M media containing xylan (1% or 5%) at 37° C. under aerobic conditions. As the cells reached the exponential growth phase ($OD_{600}$ of 0.8), induction was initiated by adding 0.2 mM IPTG. Protein expression and in situ xylan depolymerization were carried out under aerobic conditions for 24 hours after induction. In parallel, an *E. coli* strain X2S engineered for converting xylose to succinic acid was cultured overnight in glass culture tubes in LB media at 37° C., 250 rpm. The overnight culture of the X2S *E. coli* strain was centrifuged at 5000 rpm for 5 minutes and washed with M9 minimal media to avoid the carryover of nutrient traces to the next coculture stage. Coculture studies were conducted at different inoculation volume ratios of X2S to SSL26 (0.5:1; 1:1; 1.5:1; 2:1) and cultured in luer-lock tubes to produce succinic acid from xylan. The coculture was supplemented with 0.1 M $KHCO_3$ as a bicarbonate source and the CBP of xylan to succinate was carried out under microaerobic conditions for 96 hours.

As shown in FIG. 9, the volume ratio of 0.5:1 of X2S to SSL26 resulted in the greatest succinate production. The simple sugars produced in this coculture can be used in fermentation processes for production of fuels and products.

What is claimed:

1. A method of increasing extracellular endoxylanase activity in a *Bacillus subtilis* bacterium comprising:

administering a plasmid comprising:

a sequence encoding a *B. subtilis* YwmC signal peptide; and a sequence encoding an endoxylanase from *Bacillus pumilus,* wherein the sequence encoding the signal peptide is upstream of the sequence encoding the endoxylanase, thereby producing a recombinant endoxylanase modified with the signal peptide, wherein the amino acid sequence of the endoxylanase consists of SEQ ID NO:4, wherein the extracellular endoxylanase activity is increased at least 2-fold as compared to the same *B. subtilis* bacterium without the plasmid.

2. A method of producing value-added products from agricultural biomass, the method comprising:

providing an agricultural biomass, wherein the agricultural biomass comprises cellobiose and xylan;

adding a culture of a xylose producer to the agricultural biomass, wherein the xylose producer is a recombinant bacteria engineered to produce xylose from hydrolyzing the agricultural biomass, wherein the recombinant bacteria is *Bacillus subtilis*, wherein the recombinant bacteria comprises a plasmid comprising a sequence encoding a *B. subtilis* YwmC signal peptide and a sequence encoding an endoxylanase from *Bacillus pumilus*, wherein the sequence encoding the signal peptide is upstream of the sequence encoding the endoxylanase, thereby producing a recombinant endoxylanase modified with the signal peptide, and wherein the amino acid sequence of the endoxylanase consists of SEQ ID NO:4; and adding a culture of a xylose assimilator to the agricultural biomass, wherein the xylose assimilator is a bacterium selected from the group consisting of: *Escherichia coli, B. coagulans, Lactobacillus pentosus, Lactobacillus brevis*, and *Leuconostoc lactis*.

3. The method of claim 2, wherein the xylose assimilator is *E. coli*.

4. A composition comprising:

recombinant *Bacillus subtilis* engineered to produce xylose from hydrolyzing agricultural biomass, wherein the recombinant *Bacillus subtilis* comprises a plasmid comprising a sequence encoding a *B. subtilis* YwmC signal peptide and a sequence encoding an endoxylanase from *Bacillus pumilus*, wherein the sequence encoding the signal peptide is upstream of the sequence encoding the endoxylanase, thereby producing a recombinant endoxylanase modified with the signal peptide, and wherein the amino acid sequence of the endoxylanase consists of SEQ ID NO: 4; and a xylose assimilator, wherein the xylose assimilator is a bacterium selected form the group consisting of: *Escherichia coli, B. coagulans, Lactobacillus pentosus, Lactobacillus brevis*, and *Leuconostoc lactis*.

5. The composition of claim 4, further comprising a media comprising a trace metal solution and M9 media, wherein the trace metal solution comprises sulfate salts of copper, iron, zinc, and magnesium and the M9 media comprises $KH_2PO_4$, $Na_2HPO_4$, NaCl, $NH_4Cl$, glucose, tryptophan, and citrate.

* * * * *

SEQUENCE LISTING

```
Sequence total quantity: 7
SEQ ID NO: 1            moltype = AA  length = 35
FEATURE                 Location/Qualifiers
source                  1..35
                        mol_type = protein
                        organism = Bacillus subtilis
SEQUENCE: 1
MFAKRFKTSL LPLFAGFLLL FHLVLAGPAA ASAAA                         35

SEQ ID NO: 2            moltype = AA  length = 26
FEATURE                 Location/Qualifiers
source                  1..26
                        mol_type = protein
                        organism = Bacillus subtilis
SEQUENCE: 2
MKKRLIQVMI MFTLLLTMAF SADAAA                                   26

SEQ ID NO: 3            moltype = AA  length = 25
FEATURE                 Location/Qualifiers
source                  1..25
                        mol_type = protein
                        organism = Bacillus subtilis
SEQUENCE: 3
MKKRFSLIMM TGLLFGLTSP AFAAA                                    25

SEQ ID NO: 4            moltype = AA  length = 228
FEATURE                 Location/Qualifiers
source                  1..228
                        mol_type = protein
                        organism = Bacillus pumilus
SEQUENCE: 4
MNLKRLRLLF VMCIGFVLTL TAVPAHAETI YDNRIGTHGG YDFELWKDYG NTSMTLNNGG  60
AFSAQWNNIG NALFRKGKKF DSTKTHHQLG NISINYNAAF NPGGNSYLCV YGWTQSPLAE  120
YYIVESWGTY RPTGTYKGSF YADGGTYDIY ETLRVNQPSI IGDATFKQYW SVRQTKRTSG  180
TVSVSQHFRK WESLGMPMGK MYETALTVEG YRSNGSANVF TNQLMIGQ            228

SEQ ID NO: 5            moltype = AA  length = 223
FEATURE                 Location/Qualifiers
source                  1..223
                        mol_type = protein
                        organism = Trichoderma reesei
SEQUENCE: 5
MVSFTSLLAG VAAISGVLAA PAAEVESVAV EKRQTIQPGT GYNNGYFYSY WNDGHGGVTY  60
TNGPGGQFSV NWSNSGNFVG GKGWQPGTKN KVINFSGSYN PNGNSYLSVY GWSRNPLIEY  120
YIVENFGTYN PSTGATKLGE VTSDGSVYDI YRTQRVNQPS IIGTATFYQY WSVRRNHRSS  180
GSVNTANHFN AWAQQGLTLG TMDYQIVAVE GYFSSGSASI TVS                223

SEQ ID NO: 6            moltype = AA  length = 240
FEATURE                 Location/Qualifiers
source                  1..240
                        mol_type = protein
                        organism = synthetic construct
```

-continued

```
SEQUENCE: 6
DPRKDFHSQD CFLDLHLLLQ RPVIKDGYCL CVLDLCHRLC QLMRKRFMII ESAHTADTIL  60
NYGKITEIRQ HSIMAAHLAH NGTISEMLCF EKGRSLIPLK LIINLATSPS ITTQPLTQAG  120
IPTYVSTAGH NLHLNTTLLS HGALIAQQER IKDHFMPMAA HMTFMKRYVS ISLLLLETLP  180
LSNIGVYVKQ NVRAELYPSV SISENGKAVC QWGKCMKQHL KATEATEVRM CLPTSLDNNL  240

SEQ ID NO: 7           moltype = AA  length = 2499
FEATURE                Location/Qualifiers
source                 1..2499
                       mol_type = protein
                       organism = synthetic construct
SEQUENCE: 7
LSYWYDWFAQ KKLLFRTYCI VLENRLKVQS ALSHIIKASH AYLTIPESST ILHDNHHKQN  60
DVPVKIAVNI LNYLYIFLLW VEGNYYYYYL STQMKSMEKE KKHFQVVFWE TISPNHYISL  120
HQKGINHKTL SHSLQESKYQ RMFIHHQKLY KVALTYPNNL TLRRYCNQFK LYLSLSPLSL  180
RKMQGKIYIL LVLCFGIKHY QFLWLYKSFV GSNNDISLFS SNCLNQFYSS FDMPPKFLSK  240
VNLGGLLVCF LHNQSFFKSQ YYCNINIYFK NIPLYPIFVC TNGCFSRIKT TLKNVVFCVF  300
LKDLSVAKNP FLSYLDNKGN YCRSSIPTAS PVTMACCRHS PFRLRNCWEG RSVRASSLLR  360
QLAKGGCAAR RLSWVTPGFS QSRRCKTTAS EFELRPLTLI ALRSLPAFQS GNLSCQLHIG  420
QRAGRGGLRI GRQGGFSFHQ DGQQLIALHR LALRELQQAV HAGLPQQAKI LFDGGRRDIT  480
AVFGIVVSHY RDIRTNAQPG LGNGAHCAQR HLIVGNQHRS GNDALIQHLH GLLKTGHGTP  540
VAFPFRYRLN LIASEIFMPA SQTQTRRDRT WARQRDLLVT QCDQMLHAQS RTVFMGENNT  600
VDGCLVRDIK KRRNISAGSF HSNGILVIQR IVNDQPTDAL REKIVHRRFT GFDAASFYHR  660
HHHAGTQLIG ARFNRRDNLR RRVQGQTGGG NANQQRLFAR QLLCHAVGNV IQLRHRRFHF  720
FPRFRRNVAG LVHHAGNGLI RDTGILCDIV RYWFHQNRLP PFEYLIDRNQ MKHSFHYPYS  780
VMATITKQLV RTIFQPTQTS NLTNVVFESI TYVRFKCNRF FGRKPRFHRN LGTKGGKDHK  840
IFKISHWKGD MLLELRNCER ITIPIRRKDP CLESTSLITI TITITNVPGA ARLMSGLFSR  900
HASMEIFVCN KVYTLPGTNG NIRGYRLIRN SPCTNKIRWI SSVYFGRSSE RIWRLAFHNI  960
KGKNKAICSR NHGRRYSRSS KTIQPYNGID RKGGRLMVRK LGDLPRKPQG DRSSLKNPYM  1020
DLTDSESKET TEVKQTEPKR KKALLKTMKV DVSIHNKIKS LHEILAASEG NSYYLEDTIE  1080
RAIDKMVETL PESQKTFYEY ELKKRTNKGD RLQTSLFFKK YEHIYIRELR KTWEKYFKSS  1140
KNMIRLFQNM KNSVCFKNKQ KKSTRNLNLT NSGQTEKLNL RRGKGGFILV FNYLHFNILL  1200
NPIQVKILFY TVPLGDRGGT LVKTKEIQMN CIIDSKPLEI KSPGRESKKG KKKFIMLLKR  1260
KRRYGQKSKK TFLTNLVRIY LTKVIIQSII TSLIFGAIFV LKELRSMLTL VMHTAAKTFA  1320
FLVYKQSLKK WTRLLLQLEA TNCLKGTVLF GRTSVIKPRI TQRNPRFLRL DVRFLCFQKN  1380
FMETLILKFQ MTRKHMRRLK RKKRVFQRFK KSTMNLLKKW MSQKQLIFQR PYNMTQCMKI  1440
YSVKEKFEKK SKNKYLILQH LLRVYQQLKR KKSTVLKAKC KIVSLSLLLI PGLKTLRSKL  1500
KIKIVYYLYR VNLHLNGLRK DIKQLKQSLK KLDMFSKKSN EKCNKLLKYF SSFFYLEIVK  1560
KISGRYQYLM STDLNLFRLE LIINTTNNLM RDKEDTKILI SIPIKFQGGD NLIRGLSTRK  1620
DPNKIFTRVI TLINFLMGEG LKFNDKENNL LRKAFKRKEL CDAKLFTFSL TLSNSSISNC  1680
CCIIKLILFC TTFSGINTSE ACFINSGSLK SMRSIYGIAS TQVSLSASSE CFSYTSMGIS  1740
KFSSCSKVAK SLWNFLSFSS TFLSKTNTLT SESMADVFPV IISIPNLLDR NSGRKSFGER  1800
IFLCSNISDT APSKSVGEGI LPISSHFVEK SYSSIYLSYY RTVELFNQGS VLFFIILKLC  1860
SLQLDLFFQI SRVTSLADPA RGPAVRWHFS GKCARNPYLF IFLNTFKYVS AHETITLINA  1920
SIILKKEEYE YSTFPCRPYS LFCGILPSCF CSPRNAGESK RCRSVGCTSG LHRTGSQQRD  1980
PEFSPRRTFS NDEHFSSAMW RGIIPYRRAR ATRSPHTLFS ELGVLTSHRK ASYGWHDSKR  2040
IMQCCHNHEH CGQLTSDNDR RTEGANRFFA QHGGSCNSPS LGTGAESHTK RRAHHDACSN  2100
GNNVAQTINW RTTYSSFPAT INRLDGGGSC RTTSALGPSG WLVYCIWSRA WVSRYHCSTG  2160
ARWALPYRSY LHDGESGNYG TKTDRDRCLT DALVTVRPSL LIYTLDFKTS FLIKDLGEDP  2220
FSHDQNPLTV FVPLSVRPRR KDQRIFLRSF FSARNLLLAN KKTTATSGGL FAGSRATNSF  2280
SEGNWLQQSA DTKYCPSSVA VVRPPLQELC STAYIPRSAN PVTSGCCQWR VVSYRVGLKT  2340
IVTGGAAVGL NGGFVHTAQL GANDLHRTEI PTAAMRKRHA SRREKGGQVS GKRQGRNRRA  2400
HEGASRGKRL VSLSCRVSPP LTASIFVMLV RGAEPMEKRQ QRGLFTVPGL LLAFCSHVLS  2460
CVIPFCGPYY RLVSYRSPQP NDRAQRVSER GSGRAPNTH                        2499
```